US011896605B2

United States Patent
Vigsnæs et al.

(10) Patent No.: US 11,896,605 B2
(45) Date of Patent: *Feb. 13, 2024

(54) COMPOSITION COMPRISING HMSS/HMOS AND USE THEREOF

(71) Applicant: Glycom A/S, Hørsholm (DK)

(72) Inventors: Louise Kristine Vigsnæs, Copenhagen NV (DK); Bruce McConnell, La Tour de Peilz (CH); Emma Elison, Hjärup (SE)

(73) Assignee: Glycom A/S, Hørsholm (DK)

( * ) Notice: Subject to any disclaimer, the term of this patent is extended or adjusted under 35 U.S.C. 154(b) by 120 days.

This patent is subject to a terminal disclaimer.

(21) Appl. No.: 17/353,749

(22) Filed: Jun. 21, 2021

(65) Prior Publication Data

US 2021/0386766 A1    Dec. 16, 2021

Related U.S. Application Data

(63) Continuation of application No. 15/906,911, filed on Feb. 27, 2018, now Pat. No. 11,040,050, which is a continuation-in-part of application No. 15/147,115, filed on May 5, 2016, now abandoned, which is a continuation-in-part of application No. 15/034,593, filed as application No. PCT/DK2015/050332 on Oct. 29, 2015, now abandoned.

(30) Foreign Application Priority Data

Oct. 29, 2014  (DK) .............................. PA201470663

(51) Int. Cl.
*A61K 31/702* (2006.01)
*A61K 31/706* (2006.01)
*A61P 1/00* (2006.01)
*A61K 31/7016* (2006.01)

(52) U.S. Cl.
CPC ........ *A61K 31/702* (2013.01); *A61K 31/7016* (2013.01); *A61P 1/00* (2018.01)

(58) Field of Classification Search
CPC .............. A61K 31/702; A61K 31/7016; A61K 2300/00; A61P 1/00
USPC .......................................................... 514/23
See application file for complete search history.

(56) References Cited

U.S. PATENT DOCUMENTS

| 4,663,321 | A | 5/1987 | Bock et al. |
| 10,751,354 | B2 | 8/2020 | Vigsnæs et al. |
| 11,026,959 | B2 * | 6/2021 | Hennet ................. A61K 31/702 |
| 11,040,049 | B2 * | 6/2021 | McConnell ........ A61K 31/7016 |
| 11,040,050 | B2 * | 6/2021 | Vigsnæs ............. A61K 31/7016 |
| 2007/0185094 | A1 | 8/2007 | Lattmann et al. |
| 2012/0171165 | A1 * | 7/2012 | Buck .......................... A61P 1/00 514/23 |
| 2012/0171166 | A1 | 7/2012 | Chow et al. |
| 2012/0172319 | A1 | 7/2012 | Chow et al. |
| 2013/0195803 | A1 | 8/2013 | German et al. |
| 2013/0251844 | A1 * | 9/2013 | Sprenger ................. A23L 33/40 426/71 |
| 2013/0315990 | A1 * | 11/2013 | Bode ..................... A23L 33/135 536/123 |
| 2014/0249103 | A1 | 9/2014 | Buck et al. |
| 2018/0169122 | A1 | 6/2018 | Hennet et al. |
| 2018/0177809 | A1 | 6/2018 | McConnell et al. |
| 2018/0185398 | A1 | 7/2018 | Vigsnaes et al. |
| 2021/0308158 | A1 | 10/2021 | Hennet et al. |
| 2021/0308159 | A1 | 10/2021 | McConnell et al. |
| 2021/0386766 | A1 | 12/2021 | Vigsnaes et al. |

FOREIGN PATENT DOCUMENTS

| JP | 2012532195 A | 12/2013 |
| WO | 0104341 A1 | 1/2001 |
| WO | 2004026257 A2 | 4/2004 |
| WO | 2007101862 A1 | 9/2007 |
| WO | 2009131537 A1 | 10/2009 |
| WO | 2010100979 A1 | 10/2010 |
| WO | 2010115934 A1 | 10/2010 |
| WO | 2011115935 A1 | 10/2010 |
| WO | 2011005681 A1 | 1/2011 |
| WO | 2011100980 A1 | 8/2011 |
| WO | 2012007588 A1 | 1/2012 |
| WO | 2012009315 A2 | 1/2012 |
| WO | 2012092160 A2 | 7/2012 |
| WO | 2012106665 A2 | 8/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2013148134 A1 | 10/2013 |
| WO | 2013154725 A1 | 10/2013 |

(Continued)

OTHER PUBLICATIONS

Gavini et al, Microbial Ecology in Health and Disease, 2001, 13, 40-45.*

(Continued)

*Primary Examiner* — Ganapathy Krishnan
(74) *Attorney, Agent, or Firm* — Kunzler Bean & Adamson

(57) ABSTRACT

This disclosure relates generally to compositions and methods for preventing or treating mast cell mediated visceral pain.

13 Claims, No Drawings

(56) References Cited

FOREIGN PATENT DOCUMENTS

| WO | 2015077233 A1 | 5/2015 |
|---|---|---|
| WO | 2015157098 A1 | 10/2015 |

OTHER PUBLICATIONS

U.S. Appl. No. 17/353,730, "Office Action Summary", USPTO, dated Mar. 29, 2023, pp. 1-42.
Michael Camilleri, "Peripheral Mechanisms in Irritable Bowel Syndrome", N Engl J. Med. 367;17, Oct. 25, 2012, NEJM.org, pp. 1626-1635.
Thapar et al., "Diarrhoea in children: an interface between developing and developed countries", The Lancet, vol. 363, Feb. 21, 2004, www.lancet.com, pp. 641-653.
Gavini et al., "Differences in the Distribution of Bifidobacterial and Enterobacterial Species in Human *Faecal microflora* of Three Different (Children, Adults, Elderly) Age Groups", Microbial Ecology in Health and Disease 2001; 13, 40-45.
E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.
G.R. Gibson et al., "The International Scientific Association for Probiotics and Prebiotics (ISAPP) consensus statement on the definition and scope of prebiotics", Nature Reviews | Gastroenterology & Hepatology vol. 14, Aug. 2017, pp. 491-502.
J. Yang, "Lactose intolerance in irritable bowel syndrome patients with diarrhoea: the roles of anxiety, activation of the innate mucosal immune system and visceral sensitivity", Alimentary Pharmacology and Therapeutics, 2014, 39, pp. 302-311.
Longstreth et al., "Functional Bowel Disorders", Gastroenterology, 2066, p. 1480-1491, vol. 130.
Kim et al., "Methanobrevibacter smithii Is the Predominant Methanogen in Patients with Constipation-Predominant IBS and Methane on Breath", Digestive Diseases and Sciences, May 10, 2012, p. 3213-3218, vol. 57.
Qin et al., "A human gut microbial gene catalogue established by metagenomic sequencing", Nature, Mar. 4, 2010, p. 59-65, vol. 464.
Urashima et al., "Milk Oligosaccharides, Nutrition and Diet Research Progress", 2011, Nova Science Publishers, Inc.
Sikandar et al., "Visceral Pain—the Ins and Outs, the Ups and Downs", Curr Opin Support Palliat Care, 2012, p. 17-26, vol. 6.
Buhner et al., "Mast cell—nerve axis with a focus on the human gut", Biochimica et Biophysica Acta (BBA)—Molecular Basis of Disease, Jan. 2012, p. 85-92, vol. 1822-Issue 1.
Zhang et al., "Mast Cells and Irritable Bowel Syndrome: From the Bench to the Bedside", J Neurogastroenterol Motil., Apr. 2016, p. 181-192, vol. 22.
L. O'Mahony et al., "Lactobacillus and *Bifidobacterium* in Irritable Bowel Syndrome: Symptom Responses and Relationship to Cytokine Profiles", Gastroenterology 2005;128:pp. 541-551.
D. Barile et al., "Human milk and related oligosaccharides as prebiotics", Biotechnology, Feb. 19, 2013, pp. 214-219.
M. Haarman et al., Quantitative Real-Time PCR Assays To Identify and Quantify Fecal *Bifidobacterium* Species in Infants Receiving a Prebiotic Infant Formula, Applied and Environmental Microbiology, vol. 71, No. 5, May 2005, pp. 2318-2324.
N. Sprenger et al., "Longitudinal change of selected human milk oligosaccharides and association to infants' growth, an observatory, single center, longitudinal cohort study", PLOS One, Feb. 9, 2017, pp. 1-15.
U.S. Appl. No. 17/341,039 "Office Action Summary", USPTO, dated Feb. 16, 2023, pp. 1-47.
Staudacher et al., "Altered gastrointestinal microbiota in irritable bowel syndrome and its modification by diet: probiotics, prebiotics and the low FODMAP diet", Proceedings of the Nutrition Society, Feb. 24, 2016, p. 312-315, vol. 75, Issue 3.
Klindworth et al., "Evaluation of general 16S ribosomal RNA gene PCR primers for classical and next-generation sequencing-based diversity studies", Nucleic Acids Research, Jan. 1, 2013, p. e1, vol. 41 Issue 1.
Chaturvedi, P., "Milk Oligosaccharide profiles by reversed-phase HPLC of their perbenzoylated derivatives", Analytical Biochemistry, vol. 251, pp. 89-97; whole document doi:10.1006/abio.1997.2250, (Sep. 1997).
Silk, D. et al., "Clinical trial: the effects of a trans-galactooligosaccharide prebiotic on faecal microbiota and symptoms in irritable bowel syndrome", Alimentary Pharmacology & Therapeutics, doi:10.1111/j.1365-2036.2008.03911.x, (Nov. 28, 2008).
Walker M. et al., "Duodenal mastoctosis, eosinophilia and intaepithelial lymphocytosis ans possible disease markers in the irritable lowel syndrome and functional dyspepsia", Alimentary Pharmacology & Therapeutics, 29(7_765-773, doi:10.111/j.1365-2036.2009.03937.x, (Apr. 2009).
Bassett, J. et al., "A review of irritable bowel syndrome and an update on therapeutic approaches", Informa Healthcare, Expert Opin. Pharmacother, 9(7):1129-1143, doi:10.1517/14656560802048902, (2008).
Spiller R. et al., "Postinfectious irritable bowel syndrome", Gastroenterology, vol. 136, pp. 1979-1988, doi:10.1053/j.gastro.2009.02.074, (2009).
Guilatre M., et al., "Diarrheoa-predominant IBS patients show mast cell activation and hyperplasia in the jejunum", Gut, vol. 56, pp. 203-209, doi:10.1136/gut.2006.100594, (2007).
Spiller, R. et al., "Guidelines on the irritable bowel syndrome: mechanisms and practical management", Gut, vol. 56, pp. 1770-1798, doi:10.1136/gut.2007.119446, (2007).
Staudacher, H. et al., "Comparision of symptom response following advice for a diet low in fermentable carbohydrates (FODMAPs) verus standard dietary advice in patients with irritable bowel syndrome", Journal of Human Nutrition and Dietetics, vol. 24, pp. 487-495 (2011).
Shulman R. et al., "Increased gastrointestinal permeability and gut inflammation in children with functional abdominal pain and irritable bowel syndrome", J. Pediatr., 153(5):646-650, doi:10.1016/j.jpeds.2008.04.062, (Nov. 2008).
Ohman, L. et al., "Crosstalk at the mucosal border: importance of the gut microenvironment in IBS", Nat, Rev. Gastroenterol., vol. 12, pp. 36-49, doi:10.1038/nrgastro.2014.200, (Jan. 2015).
Schoepfer, A. et al., "Antibodies to flagellin indicate reactivity to bacterial antigens in IBS patients", Neurogastroenterol Motil, vol. 20, pp. 1110-1118, doi:10.1111/j.1365-2982.2008.01166.x, (2008).
Kerckhoffs, A. et al., "Lower bifidobacteria counts in both duodenal mucosa-associated and fecal microbiota in irritable bowel syndrome patients", World J. Gastroenterol, 15(23):2887-2892, doi:10.3748/wjg.15.2887, (Jun. 21, 2009).
Jeffrey, I. et al., "An irritable bowel syndrome subtype defined by species-specific alterations in faecal microbiota", Gut 2012, 61:997-1006, published on Dec. 16, 2011, doi:10.1136/gutjnl-2011-301501, pp. 997-1006.
Rockova, S. "Inter-species differences in the growth of bifidobacteria cultured on human milk oligosaccharides", Folia Microbiologica, 2012, vol. 57, No. 4, Apr. 11, 2012, pp. 321-324.
Heitkemper, M. "Update on Irritable Bowel Syndrome Program of Research", J Korean Academy of Nursing vol. 43 No. 5, 579-586, http://dx.doi.org/10.4040/jkan.2013.43.5.579, Sep. 23, 2013, pp. 579-586.

* cited by examiner

COMPOSITION COMPRISING HMSS/HMOS AND USE THEREOF

CROSS-REFERENCES TO RELATED APPLICATIONS

This is a continuation of and claims priority to U.S. patent application Ser. No. 15/906,911 titled "Composition Comprising HMSs/HMOs and use thereof" and filed on Feb. 27, 2018, which is a continuation-in-part application of and claims priority to U.S. patent application Ser. No. 15/147,115 titled "Composition Comprising HMSs/HMOs and use thereof" and filed on May 5, 2016, which is a continuation application of and claims priority to U.S. patent application Ser. No. 15/034,593 titled "Synthetic composition and method for treating irritable bowel syndrome", filed on May 5, 2016, which is a national stage filing in accordance with 35 U.S.C. § 371 of PCT/DK2015/050332 filed Oct. 29, 2015, which claims the benefit of the priority of Denmark Patent Application No. PA 2014 70663, filed Oct. 29, 2014, all of which are incorporated herein by reference to the extent legally allowable.

FIELD

This disclosure relates generally to compositions and methods for preventing or treating mast cell mediated visceral pain.

BACKGROUND

Visceral hypersensitivity and pain represent a major clinical problem, yet far less is known about its mechanisms compared to somatic pain. Visceral hypersensitivity and pain are defined as pain felt arising from the internal organs (viscera) of the body. There are multiple etiologies for pain sensed in viscera, including inflammation (acute and chronic), infection, disruption of normal mechanical processes (e.g., gastrointestinal dysmotility) or alterations in nerves. The recent growth in interest in pain originating from internal organs reflects an important paradigm shift in the awareness of the magnitude and impact of visceral pain disorders.

Visceral pain usually has a temporal evolution and clinical features vary in different phases of pathology. 'True visceral pain' arises as a diffuse and poorly defined sensation usually perceived in the midline of the body, at the lower sternum or upper abdomen. In patients, pain from different visceral organs can have differing areas of presentation, e.g., bladder to perineal area, heart to left arm and neck, left ureter to left lower quadrant and loin. This diffuse nature and difficulty in locating visceral pain is due to a low density of visceral sensory innervation and extensive divergence of visceral input within the central nerve system. Visceral pain is therefore perceived more diffusely than noxious cutaneous stimulation with respect to location and timing. Visceral pain is often associated with marked autonomic phenomena, including pallor, profuse sweating, nausea, gastrointestinal disturbances and changes in body temperature, blood pressure and heart rate (Sikandar et al. Curr. Opin. Support. Palliat. Care 6, 17 (2012)).

Mast cells are believed to play an important role in the pathogenesis of IBS. Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by bacteria in both post-infectious IBS and non-post-infectious IBS.

Therefore, there is a need for a safe, effective intervention for the treatment of visceral pain disorders mediated by mast cells.

SUMMARY

A method is disclosed for reducing mast cell mediated visceral hypersensitivity and/or pain in a non-infant human. In various examples, the method includes: selecting an effective amount of one or more neutral human milk oligosaccharides (HMOs) chosen from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human; and increasing the relative abundance of *Bifidobacterium adolescentis* in the gastrointestinal microbiota of the non-infant human and reducing the mast cell mediated visceral hypersensitivity and/or pain by administering to the non-infant human a daily dose of the selected effective amount of the HMOs in the mixture.

In certain examples, the non-infant human has intestinal bacterial overgrowth, dysbiosis and/or an impaired mucosal barrier. In some examples, the non-infant human is an irritable bowel syndrome (IBS) patient. In various examples, administering the chosen one or more neutral HMOs includes administering a mixture of: one or more fucosylated neutral HMOs selected from 2'-FL, 3-FL, DFL, and LNFP-I; and one or more non-fucosylated neutral HMOs selected from LNT and LNnT.

In various examples, the mass ratio of the fucosylated neutral HMOs to the non-fucosylated neutral HMOs in the mixture is from 4:1 to 2:1. In some examples, administering the chosen one or more neutral HMOs includes administering a mixture of: one or more fucosylated neutral HMOs selected from 2'-FL, 3-FL, DFL, and LNFP-I; and one or more non-fucosylated neutral HMOs selected from LNT and LNnT.

In some examples, the method includes administering with the selected effective amount of the mixture, one or more additional HMOs selected from the group consisting of 3'-sialyllactose (3'-SL) and 6'-sialyllactose (6'-SL).

In certain examples, the method further includes including improving the gut barrier function of the non-infant human patient by administering to the non-infant human the selected effective amount of the mixture.

In various examples, the method includes reducing the looseness and/or frequency of bowel movements of the non-infant human by administering to the non-infant human the selected effective amount of the mixture.

In some examples, the daily dose of the chosen one or more HMOs is from about 5 g to 10 g for an initial treatment period of 1 to 8 weeks, followed by from about 1 g to 5 g for a maintenance period of at least 1 month.

A further method is disclosed for reducing mast cell mediated visceral hypersensitivity and/or pain in a non-infant human. In some examples, the method includes: selecting an effective amount of one or more neutral human milk oligosaccharides (HMOs) chosen from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human; increasing the relative abundance of *Bifidobacterium adolescentis* in the gastrointestinal microbiota of the non-infant human and reducing the mast cell mediated visceral hypersensitivity and/or pain by administering to the non-infant human a daily dose of the selected effective amount of the chosen one or more neutral HMOs; and selectively increasing the expression of intestinal goblet cell genes to improve mucosal barrier function in gastrointestinal tract of the non-infant human by administering to the non-infant human a daily dose of the selected effective amount of the chosen one or more neutral HMOs.

In certain examples, selectively increasing the expression of the intestinal goblet cell genes includes selectively increasing the expression of MUC2 and/or TTF3 genes relative to the expression of CHST5 or GAL3ST2 goblet cell genes.

In some examples, the amount of the daily dose of the chosen one or more HMOs is from about 5 g to 10 g for an initial treatment period of 1 to 8 weeks, followed by from about 1 g to 5 g for a maintenance period of at least 1 month.

DETAILED DESCRIPTION

Reference throughout this specification to "one example," "an example," or similar language means that a particular feature, structure, or characteristic described in connection with the example is included in at least one example of the present disclosure. Thus, appearances of the phrases "in one example," "in an example," and similar language throughout this specification may, but do not necessarily, all refer to the same example.

Furthermore, the described features, structures, or characteristics of the disclosure may be combined in any suitable manner in one or more examples. One skilled in the relevant art will recognize, however, that the disclosure may be practiced without one or more of the specific details, or with other methods, components, materials, and so forth. In other instances, well-known structures, materials, or procedures are not shown or described in detail to avoid obscuring aspects of the disclosure.

Introduction

The "brain-gut axis" is a theoretical model depicting bidirectional neural pathways linking cognitive, emotional and autonomic centres in the brain to neuroendocrine centres, the enteric nervous system and the immune system. The gastrointestinal tract possesses both the largest neural network outside the brain and the most extensive immune system, which brings about the opportunity for crosstalk between neurons and immune cells, including mast cells. Many studies have confirmed that endings of postganglionic sympathetic, peptidergic and vagal fibres, and enteric neurons are in close proximity to mast cells. It has been estimated that 70% of intestinal mucosal mast cells are in direct contact with nerves. Due to their location mast cells play an important role in the regulation of gastrointestinal visceral hypersensitivity and vascular permeability, and an alteration in the mast cells—nerve axis can contribute to autonomic dysregulation of the gut and associated pain and perceptual changes in visceral disorders. Several studies have noted an increased number of mast cells in the mucosa of patients with gastrointestinal diseases such as irritable bowel syndrome, mastocytic enterocolitis, and systemic mastocytosis (Buhner et al. *Biochim. Biophys. Acta* 1822, 85 (2012)).

The functional mast cell-neuronal units consist of 2 pathways: the nerve to mast cells signalling and the mast cells to nerve signalling. One of the important mediators in this process is mast cell tryptase, which activate Protease-activated Receptor 2 (PAR2) present on sensory afferents. PAR2 plays a crucial role in sensitizing afferent neurons and also causes the release of substance P (SP) and Calcitonin gene-related peptide (CGRP). This system acts to amplify the inflammatory response with the gastrointestinal tract and leads to increased motility and secretion as part of the enteric nervous system (ENS) response to mast cell degranulation. Mast cells hyperplasia and activation can lead to abnormal gastrointestinal sensitivity, motility, and secretion, which in turn contribute to the hallmark symptoms found in functional gastrointestinal disorders including abdominal pain and/or discomfort, bloating, and abnormal bowel function (diarrhoea and/or constipation) (Zhang et al. *J. Neurogastroenterol. Motil.* 22, 181 (2016)).

Beside the mast cells—nerve axis, emerging data show that there is an interaction between the intestinal microbiota and pathways mediating visceral pain. The absence of gastrointestinal bacteria, such as which occurs in germ free mice, is associated with reduced perception of pain following different inflammatory stimuli. Furthermore, modulation of the intestinal microbiota by administration of various probiotics or prebiotics also has been shown to alter pain responses.

Visceral pain is one of the defining criteria for irritable bowel syndrome (IBS). Irritable bowel syndrome is a clinically heterogeneous disorder of human patients, particularly adult, with chronic symptoms such as abdominal pain, abdominal discomfort, abdominal bloating, fatigue, and changes in bowel movement patterns, such as patterns of loose or more frequent bowel movements, diarrhea and constipation. Routine clinical tests on patients typically show no abnormalities, although their bowels may be more sensitive to certain stimuli, such as balloon insufflation testing. The worldwide prevalence of IBS is about 10-20% but may be higher in certain countries (Longstreth et al. *Gastroenterology* 130, 1480 (2006)). The causes of IBS are unknown but disruptions of the brain-gut axis, acute gastrointestinal infections, small intestinal bacterial overgrowths, antibiotic usages and dysbiosis are thought to be important risk factors (Kim et al. *Dig. Dis. Sci.* 57, 3213 (2012)). Other risk factors are young age, prolonged fever, anxiety, and depression. Chronic low-grade inflammation commonly occurs in IBS patients, but there are otherwise little or no observable clinical manifestations.

Diagnosis of IBS is difficult. No biomarker-based tests can be performed to diagnose IBS. Diagnosis generally involves excluding conditions that produce IBS-like symptoms and then following a procedure to categorise a patient's symptoms. Ruling out parasitic infections, lactose intolerance, and celiac disease is recommended for all patients before a diagnosis of IBS is made. Once diagnosed, patients are usually classified in accordance with the Rome III criteria into four symptom subtypes based on stool consistency: diarrhea predominant (IBS-D), constipation predominant (IBS-C), mixed subtype (IBS-M) with alternating episodes of both diarrhea and constipation, and unsubtyped IBS (IBS-U).

There is no cure for IBS and current treatments focus on attempting to relieve symptoms; including visceral pain but current pain treatments have limited efficacy. Treatments take various forms such as dietary adjustments, medication, and psychological interventions. Patient education and good doctor-patient relationships are also important. However, most treatment is unsatisfactory and most patients continue to experience chronic pain, fatigue, and other symptoms. While IBS has no direct effect on life expectancy, its high prevalence and significant effects on quality of life make it a condition with a high social cost. The general hopelessness associated with IBS is a source of frustration for both patients and health care practitioners treating them.

Current research has implicated the gastrointestinal microbiota, the brain-gut axis and the mast cells in the pathophysiology of IBS. The human gastrointestinal microbiota includes at least 1,000 species of bacteria, and about $10^{14}$ individual bacterial cells from about 160 different species inhabit each individual's intestine (Qin et al. *Nature* 464, 59 (2010)). It is believed that an individual's genetic make-up and acquired immunity, as well as environmental factors, influence their gastrointestinal microbiota. The microbiota in turn shape the individual's immunity and physiology within the gastrointestinal system. It is also believed that a healthy individual maintains a symbiotic relationship with the microbiota colonizing his/her intestines, while an individual with IBS has an imbalance in this microbiota-host interaction.

Thus, a composition and method using selected HMOs for treatment of the underlying causes of visceral pain disorders mediated by mast cells that is safe, effective, and convenient to administer would be beneficial.

The present disclosure has been developed in response to the present state of the art, and in particular, in response to the problems and needs in the art that have not yet been fully solved by currently available treatments.

Provided herein are synthetic compositions comprising one or more human milk monosaccharides (HMSs) or one or more human milk oligosaccharides (HMOs), or both, that can be advantageously used for the prophylaxis or treatment of mast cell mediated visceral hypersensitivity and/or pain in a human, in particular a non-infant human individual. In one example, the human is an irritable bowel syndrome patient. The patient may have intestinal dysbiosis and/or an impaired mucosal barrier.

A first aspect of this disclosure relates to a human milk mono- or oligosaccharide or a mixture of human milk mono- and/or oligosaccharides for the prophylaxis or treatment of mast cell mediated visceral hypersensitivity and/or pain in a human. A second aspect of this disclosure relates to a synthetic composition for the prophylaxis or treatment of mast cell mediated visceral hypersensitivity and/or pain in a human, the composition comprising an effective amount of one or more human milk monosaccharides or one or more human milk oligosaccharide. A third aspect of this disclosure relates to a method for the prophylaxis or treatment of mast cell mediated visceral hypersensitivity and/or pain in a human, the method comprising administering to the human an effective amount of one or more human milk monosaccharides or one or more human milk oligosaccharide.

The amount of a human milk mono- and/or oligosaccharide may be effective to (i) increase the abundance, particularly the relative abundance, of bifidobacteria, and/or (ii) improve the gut barrier function of the human. The bifidobacteria increased may be a member of the phylogenetic *Bifidobacterium adolescentis* group, for example *Bifidobacterium pseudocatenulatum* and/or *Bifidobacterium adolescentis*.

In certain examples the human milk oligosaccharide is 2'-FL, 3-FL, DFL, LNnT, LNT, 3'-SL, 6'-SL or LNFP-I or a mixture thereof. For example, the composition may comprise a mixture of a fucosylated HMO such as 2'-FL and a non-fucosylated neutral HMO such as LNnT or LNT, or both. 2'-FL and LNnT/LNT may be present in a mass ratio of about 5:1 to 1:1 or about 4:1 to 2:1.

The synthetic composition can be a nutritional or pharmaceutical composition. A synthetic composition of the disclosure is sometimes administered daily. Furthermore, the synthetic composition may be administered for a period of at least one month, such as at least 2 months or for a longer period of time, for example chronically on an on-going basis.

The synthetic composition may be administered to the human or patient as a daily dose of about 3 g to about 15 g such as from about 3 g to about 10 g of HMSs and/or HMOs. The patient may be administered a higher amount, preferably 5 g to 10 g per day, of the HMSs and/or HMOs for an initial treatment period, followed by a lower amount, preferably 3 g to 5 g per day, for a maintenance period. The initial treatment period may be 1 to 8 weeks. In some examples the maintenance period is at least 1 month.

Reference throughout this specification to features, advantages, or similar language does not imply that all of the features and advantages that may be realized with the present disclosure should be or are in any single example of the disclosure. Rather, language referring to the features and advantages is understood to mean that a specific feature, advantage, or characteristic described in connection with an example is included in at least one example of the present disclosure. Thus, discussion of the features and advantages, and similar language, throughout this specification may, but do not necessarily, refer to the same example.

Furthermore, the described features, advantages, and characteristics of the disclosure may be combined in any suitable manner in one or more examples. One skilled in the relevant art will recognize that the disclosure may be practiced without one or more of the specific features or advantages of a particular example. In other instances, additional features and advantages may be recognized in certain examples that may not be present in all examples of the disclosure.

These features and advantages of the present disclosure will become more fully apparent from the following description and appended claims, or may be learned by the practice of the disclosure as set forth hereinafter.

Human milk monosaccharides (HMSs) and/or human milk oligosaccharides (HMOs) have been shown to modulate the gut microbiota, stabilize mast cells and hereby prevent symptoms in patients suffering from visceral pain. HMSs and/or HMOs preferentially increase the abundance of beneficial bacteria, such as bifidobacteria, and regulate immune responses causing a decrease in the degranulation and activation of mast cells. Furthermore, HMSs and/or HMOs act to repair damage in the mucosal barrier and act on neuronally dependent gut migrating motor complexes to address disorders of gut motility and possibly have beneficial effects on the central nervous systems of patients. As an outcome, visceral hypersensitivity and/or pain may be reduced.

The term "oral administration" means any conventional form for the oral delivery of a composition to a patient that causes the deposition of the composition in the gastrointestinal tract (including the stomach) of the patient. Accordingly, oral administration includes swallowing of composition by the patient, enteral feeding through a naso-gastric tube, and the like.

The term "effective amount" means an amount of a composition that provides a human milk monosaccharide or human milk oligosaccharide in a sufficient amount to render a desired treatment outcome in a patient. An effective amount can be administered in one or more doses to the patient to achieve the desired treatment outcome.

The term "human milk monosaccharide" or "HMS" means a monosaccharide found in human breast milk. Examples include sialic acid and L-fucose. In human milk, the sialic acid is N-acetylneuraminic acid.

The term "human milk oligosaccharide" or "HMO" means a complex carbohydrate found in human breast milk that can be in acidic or neutral form. More than about 200 different HMO structures are known to exist in human breast milk (Urashima et al.: *Milk Oligosaccharides*, Nova Biomedical Books, New York, 2011). HMOs can be backbone, fucosylated and sialylated oligosaccharides. Backbone HMOs consists of Glu, Gal and GlcNAc and are devoid of Fuc and sialic acid. Examples of backbone HMOs include lacto-N-tetraose (LNT), lacto-N-neotetraose (LNnT), lacto-N-neohexaose (LNnH) and lacto-N-hexaose (LNH). Fucosyl HMOs are fucosylated lactoses or fucosylated backbone HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated backbone HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialyl and fucosyl HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The terms "microbiota", "microflora" and "microbiome" mean a community of living microorganisms that typically inhabits a bodily organ or part. Dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level the microorganisms of *Bacteroides, Faecalibacterium, Bifidobacterium, Roseburia, Alistipes, Collinsella, Blautia, Coprococcus, Ruminococcus, Eubacterium* and *Dorea*; and at species level microorganisms of *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The terms "irritable bowel syndrome" and "IBS" mean a group of functional bowel disorders of humans, particularly adults, characterized by one or more chronic symptoms including abdominal pain, abdominal discomfort, abdominal bloating, fatigue, and changes in bowel movement patterns, such as patterns of loose or more frequent bowel movements, diarrhoea and constipation, typically in the absence of any apparent structural abnormality. There are at least three forms of IBS, depending on which symptom predominates: (1) diarrhoea-predominant (IBS-D); (2) constipation-predominant (IBS-C); and (3) IBS with alternating stool pattern (IBS-A or IBS-M). There are also various clinical subtypes of IBS, such as post-infectious IBS (IBS-PI).

The term "bifidobacteria" means a member of the *Bifidobacterium* genus commonly found in the human gastrointestinal tract. Examples of bifidobacteria are: *Bifidobacterium longum, Bifidobacterium bifidum*, and members of the phylogenetic *Bifidobacterium adolescentis* group. In non-infant humans, bifidobacteria preferably include members of the phylogenetic *Bifidobacterium adolescentis* group, for example *Bifidobacterium pseudocatenulatum* and/or *Bifidobacterium adolescentis*.

The term "synthetic composition" means a composition which is artificially prepared and preferably means a composition containing at least one compound that is produced ex vivo chemically and/or biologically, e.g., by means of chemical reaction, enzymatic reaction or recombinantly. In some examples a synthetic composition may be, but preferably is not, identical with a naturally occurring composition. The synthetic composition typically comprises one or more HMSs and/or HMOs that are capable of preferentially increasing the abundance of bifidobacteria. In some examples, the synthetic composition may comprise one or more compounds or components other than HMSs and/or HMOs that may have an effect on bifidobacteria of a human subject microbiota in vivo, e.g., non-digestible oligosaccharides or prebiotics. Also in some examples, the synthetic compositions may comprise one or more nutritionally or pharmaceutically active components which do not affect adversely the efficacy of the above-mentioned compounds. Some non-limiting examples of a synthetic composition of the disclosure are also described below. The synthetic composition preferably comprises an effective amount of one or more HMS, HMO or both.

The term "effective amount" means an amount of a human milk mono- and/or oligosaccharide per administration dose which is effective to (i) increase the abundance, particularly a relative abundance, of bifidobacteria, and/or (ii) improve the gut barrier function of the human. The bifidobacteria increased may be a member of the phylogenetic *Bifidobacterium adolescentis* group, for example *Bifidobacterium pseudocatenulatum* and/or *Bifidobacterium adolescentis*. The effective amount of HMS(s) and HMO(s) may vary depending on compound selected from the groups of HMSs and HMOs described herein. The effective amount may be in the range from about 1 to about 10 g or more of HMS and/or HMOs per administration dose; in some preferred examples, the effective amounts are from about 3 to about 10 g per administration dose.

Definitions

The following definitions apply to the present disclosure unless otherwise clear from context:

The term "relative abundance of bifidobacteria" means the abundance of bifidobacteria relative to other genera in the microbiota of the gastro-intestinal tract.

The term "relative growth of bifidobacteria" means the growth of bifidobacteria relative to other genera of bacteria in the microbiota in the gastro-intestinal tract.

The term "non-infant human" or "non-infant" means in the present context a human of 3 years of age and older. A non-infant human can be a child, a teenager, an adult or an elderly.

The term "enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

The term "oral administration" means any conventional form for the delivery of a composition to a human through the mouth. Accordingly, oral administration is a form of enteral administration.

The term "visceral hypersensitivity" refers to an increased intensity of sensation of stimuli of visceral organs of the body.

The "visceral organ" is an organ of the digestive, respiratory, urogenital and endocrine systems as well as the spleen, the heart and great vessels. In particular, a person who experiences visceral hypersensitivity may have a lowered threshold for visceral pain, such as abdominal pain and discomfort in response to pressure, stimulation or distension within the abdomen.

The term "visceral pain" refers to a distressing feeling arising from the visceral organs of the body.

The term "about" in the present context means up to 2.5% deviation from the corresponded value.

HMSs and/or HMOs for Prophylaxis or Treatment of Mast Cell Mediated Visceral Hypersensitivity and/or Pain in a Human HMSs and/or HMOs for prophylaxis or treatment of mast cell mediated visceral hypersensitivity and/or pain in a human may be a single HMS, a mixture of HMSs, a single HMO, a mixture of any HMOs or a mixture of one or more HMSs and one or more HMOs suitable for the purpose of the disclosure. The HMS may be L-fucose or sialic acid, and the HMO is a fucosylated or a non-fucosylated neutral HMO. The HMSs and/or HMOs for prophylaxis or treatment of mast cell mediated visceral hypersensitivity and/or pain in a human may be a mixture of at least a first HMO, at least a second HMO and optionally L-fucose and/or sialic, wherein the first HMO is a fucosylated neutral HMO and the second HMO is a non-fucosylated neutral HMO. Particularly, the mixture may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. In certain examples the mixture contains a fucosylated HMO selected from the list consisting of 2'-FL, 3-FL and DFL, and a non-fucosylated HMO selected from the list consisting of LNT and LNnT. The mixture sometimes comprises 2'-FL and LNnT and/or LNT. In some examples, the mixture may essentially consist of two neutral HMOs, e.g., a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. The mixture sometimes essentially consists of a fucosylated HMO selected from the list consisting of 2'-FL, 3-FL and DFL, and a non-fucosylated HMO selected from the list consisting of LNT and LNnT; in one preferred example the mixture essentially consists of 2'-FL and LNnT, in another preferred example the mixture essentially consists of 2'-FL and LNT.

The HMOs can be isolated or enriched by well-known processes from milk(s) secreted by mammals including, but not limited to human, bovine, ovine, porcine, or caprine species. The HMOs may also be produced by well-known processes using microbial fermentation, enzymatic processes, chemical synthesis, or combinations of these technologies. As examples, using chemistry LNnT may be made as described in WO 2011/100980 and WO 2013/044928, LNT may be synthesized as described in WO 2012/155916 and WO 2013/044928, a mixture of LNT and LNnT can be made as described in WO 2013/091660, 2'-FL may be made as described in WO 2010/115934 and WO 2010/115935, 3-FL can be made as described in WO 2013/139344, 6'-SL and salts thereof may be made as described in WO 2010/100979, sialylated oligosaccharides may be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides may be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

Synthetic Composition Comprising HMSs and/or HMOs

The synthetic composition may comprise a single HMS, a mixture of HMSs, a single HMO, a mixture of any HMOs or a mixture of one or more HMSs and one or more HMOs suitable for the purpose of the disclosure. In certain examples the HMS is L-fucose or sialic acid, and the HMO is a fucosylated or a non-fucosylated neutral HMO. The composition sometimes comprises a mixture of at least a first HMO, at least a second HMO and optionally L-fucose and/or sialic, wherein the first HMO may be a fucosylated neutral HMO and the second HMO may be a non-fucosylated neutral HMO. Particularly, the composition may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. The composition may contain a fucosylated HMO selected from the list consisting of 2'-FL, 3-FL and DFL, and a non-fucosylated HMO selected from the list consisting of LNT and LNnT. The composition sometimes comprises 2'-FL and LNnT and/or LNT. In some examples, the composition comprises a mixture essentially consists of two neutral HMOs, e.g., a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. In various examples the composition comprises a mixture consisting of a fucosylated HMO selected from the list consisting of 2'-FL, 3-FL and DFL, and a non-fucosylated HMO selected from the list consisting of LNT and LNnT. The composition may comprise a mixture essentially consisting of 2'-FL and LNnT. In some examples the composition comprises a mixture essentially consisting of 2'-FL and LNT.

A synthetic composition of this disclosure comprising one or more human milk monosaccharides, or one or more human milk oligosaccharides, or both, may take any suitable form. For example, the composition may be in the form of a nutritional composition which contains other macronutrients such as proteins, lipids or other carbohydrates. The synthetic composition can also be a pharmaceutical composition or other unit dose form.

Nutritional Compositions

A nutritional composition of this disclosure may contain sources of protein, lipids and/or digestible carbohydrates and may be in powdered or liquid forms. The composition may be designed to be the sole source of nutrition or a nutritional supplement. For visceral pain patients, a nutritional supplement may be beneficial; especially a supplement which can form a meal or snack replacement. The nutritional composition may be lactose-reduced or lactose-free. The nutritional composition may also be free from, or low in amounts of, FODMAP carbohydrates.

Suitable protein sources include without limitation milk proteins, soy protein, rice protein, pea protein and oat protein, or mixtures thereof. Milk proteins may be in the form of milk protein concentrates, whey protein or casein, or mixtures of both. Soy, rice, pea and oat protein may be in the form or protein isolated. The protein may be whole protein or hydrolysed protein, either partially hydrolysed or extensively hydrolysed. The protein may provide about 5% to about 50%, preferably about 10% to 30%, of the energy of the nutritional composition. The protein source preferably is not a source of non-fermentable carbohydrates such as lactose. Therefore, if a milk protein is used as the protein source, the milk protein is preferably lactose-reduced or lactose-free.

The protein source may be a source of glutamine, threonine, cysteine, serine, proline, or a combination of these amino acids. The glutamine source may be a glutamine dipeptide and/or a glutamine enriched protein. Glutamine may be included due to the use of glutamine by enterocytes as an energy source. Threonine, serine and proline are important amino acids for the production of mucin. Mucin coats the GI tract and can reduce permeability. Cysteine is a major precursor of glutathione, which is key for the antioxidant defences of the body.

Suitable digestible carbohydrates include without limitation maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include without limitation rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), may be included in the lipid source because they have anti-inflammatory properties. Suitable sources of LC-PUFA are plant oils, marine plankton oils, fungal oils, and fish oils. The lipid source may also include medium chain triglycerides (MCT). Fractionated coconut oils are a suitable source of medium chain triglycerides. The lipid source preferably provides about 5% to about 25% of the energy of the nutritional composition; for example, about 10% to 20%. In various examples the lipid content is reduced because high fat diets can provoke IBS symptoms.

The nutritional composition may also include vitamins and minerals. If the nutritional composition is intended to be a sole source of nutrition, it may beneficially include a vitamin and mineral profile, including a complete vitamin and mineral profile. The term "complete" in the present context means a vitamin and mineral profile comprising all vitamins and minerals essential for body function, wherein the essential vitamins includes at least 9 vitamins from the exemplary group below, such as 10, 11, 12 or 13, or more, and the essential minerals includes at least 5 minerals from the exemplary group below, such as from 6 to 13 or more. Examples of vitamins include without limitation vitamins A, B-complex (such as B1, B2, B6 and B12), C, D, E and K, niacin and acid vitamins such as pantothenic acid and folic acid and biotin. Examples of minerals include without limitation calcium, iron, zinc, magnesium, iodine, copper, phosphorus, manganese, potassium, chromium, molybdenum, selenium, nickel, tin, silicon, vanadium and boron.

The nutritional composition may also include without limitation a carotenoid such as lutein, lycopene, zeaxanthin, and beta-carotene. The total amount of carotenoid included may vary from about 0.001 µg/ml to about 10 µg/ml. Lutein may be included in an amount of from about 0.001 µg/ml to about 10 µg/ml, sometimes from about 0.044 µg/ml to about 5 g/ml of lutein. Lycopene may be included in an amount from about 0.001 µg/ml to about 10 µg/ml, in some examples about 0.0185 mg/ml to about 5 g/ml of lycopene. Beta-carotene may comprise from about 0.001 µg/ml to about 10 mg/ml, for example about 0.034 µg/ml to about 5 µg/ml of beta-carotene.

The nutritional composition may also contain various other conventional ingredients such as, without limitation, preservatives, emulsifying agents, thickening agents, buffers, fibres and probiotics, especially probiotics which can help to reduce symptoms in IBS patients (e.g., VSL #3, *B. infantis* 35624, *B. animalis* sub sp. *lactis* BB-12, *B. lactis* Bi-07, *L. rhamnosus* GG, *L. rhamnosus* Lc705, *L. plantarum* DSM 9843, *L. plantarum* CECT7484, *L. plantarum* CECT7485, *L. acidophilus* NCFM, *L. fermentum* CECT5716, *B. breve* Bb99, *Propionibacterium freundenreichii* ssp. *Shermanii* JS, *P. acidilactici* CECET7483, *Streptococcus faecium*), antioxidant/anti-inflammatory compounds including tocopherols, carotenoids, ascorbate/vitamin C, ascorbyl palmitate, polyphenols, glutathione, and superoxide dismutase (melon), other bioactive factors (e.g., growth hormones, cytokines, TFG-β), colorants, flavours, and stabilisers, lubricants, and so forth.

The nutritional composition may be in the form of a soluble powder, a liquid concentrate, or a ready-to-use formulation. Various flavours, fibres and other additives can also be present.

The nutritional compositions may be prepared by any commonly used manufacturing techniques for preparing nutritional compositions in solid or liquid form. For example, the composition can be prepared from various feed solutions. A protein-in-fat feed solution may be prepared by heating and mixing the lipid source and then adding an emulsifier (e.g., lecithin), fat soluble vitamins, and at least a portion of the protein source while heating and stirring. A carbohydrate feed solution is also prepared by adding minerals, trace and ultra-trace minerals, thickening or suspending agents to water while heating and stirring. The resulting solution is held for 10 minutes with continued heat and agitation before adding carbohydrates (e.g., the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range, if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively, the composition can be spray dried and processed and packaged as a reconstitutable powder.

When the nutritional product is a ready-to-feed nutritional liquid, the total concentration of HMOs in the liquid, by weight of the liquid, may be from about 0.02% to about 2.0%, including from about 0.1% to about 1.5%, including from about 0.3% to about 1.0%. When the nutritional product is a concentrated nutritional liquid, the total concentration of HMOs in the liquid, by weight of the liquid, may be from about 0.04% to about 4.0%, including from about 0.2% to about 3.0%, including from about 0.6% to about 2.0%.

Unit Dosage Forms

The synthetic composition may also be in a unit dosage form such as a capsule, tablet or sachet. For example, the composition may be in a tablet form comprising the human milk mono- and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include without limitation polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, may also include various nutrients including macronutrients.

The unit dosage forms may be administered orally, e.g., as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions may include without limitation binders, lubricants, inert diluents, flavouring agents, and humectants. Orally administered compositions such as tablets can optionally be coated and may be formulated so as to provide sustained, delayed or controlled release of the mixture therein.

The unit dosage forms may also be administered by rectal suppository, aerosol tube, naso-gastric tube or direct infusion into the GI tract or stomach.

The unit dosage forms may also include therapeutic agents such as antiviral agents, antibiotics, probiotics, analgesics, and anti-inflammatory agents. The synthetic composition in unit dosage form may be a pharmaceutical composition or a nutritional supplement.

Administration Dosing

For reducing symptoms of visceral pain in a patient, the amount of HMS(s) and/or HMO(s), preferably HMO(s), required to be administered to the patient may vary depending upon factors such as the risk and severity of the disease, the age of the patient, the form of the composition, and other medications being administered to the patient. However, the required amount may be readily set by a medical practitioner and could generally be in the range from about 200 mg to about 20 g per day, in certain examples from about 1 g to about 15 g per day, from about 3 g to about 10 g per day, in certain examples from about 3 g to about 7.5 g per day. An appropriate dose may be determined based on several factors, including, for example, body weight and/or condition, the severity of the condition, being treated or prevented, other ailments and/or diseases, the incidence and/or severity of side effects and the manner of administration. Appropriate dose ranges may be determined by methods known to those skilled in the art. During an initial treatment phase, the dosing may be higher or lower depending upon the need to boost bifidobacteria WE abundance or initial tolerance to HMSs/HMOs. During a maintenance phase, the dosing may be set for chronic long-term use.

The duration of the HMS/HMO administration may vary depending upon factors such as the risk and severity of the medical condition, age, the form of the composition, the dose and other medications being administered. However, the duration can be readily set by a medical practitioner. Generally, a duration of at least a week will be required to sufficiently to impact symptoms. For example, the duration may be for 1 to 3 months. The administration may continue chronically for an indefinite period.

EXAMPLES

Examples are to illustrate non-limiting examples the disclosure.

Example 1—Human Trial

A total of 60 male and female IBS patients are recruited to participate in the study. After a screening visit and run-in period of 1-2 weeks, the patients are selected. The patients are randomized into three groups, each of 20 patients, with two groups consuming the treatment product and one group the placebo product for 8 weeks. The treatment product contain either 5 or 10 grams of a combination of 2'-FL and LNnT in a 4:1 ratio, while the placebo product contain 2 grams of glucose. Both products are in powder form in a unit dosage container.

The patients are eligible to participate if they are at least 18 years of age and meet the Rome III criteria for LBS. All recruited patients are able and willing to understand and comply with the study procedures. Patients are excluded if: they have participated in a clinical study one month prior to screening visit; they have abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and are pregnant or lactating.

At the screening visit, medical history and concomitant medication are registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or control products. Subjects are reminded not to change their usual diet during the study. Blood samples are collected for biomarker studies.

The serum from the blood samples is transferred to cryotubes and stored at −80° C. The following biomarkers are measured: aldosterone, angiotensin II, ApoA1, ApoB, blood urea nitrogen, iron, brain natriuretic peptide (BNP), cortisol, Eosinophilic cationic protein (ECP), estradiol, aliphatic carboxylate (FFA), glucagon, HbA1c, IgA, IgM, IgG, IL-10, IL-6, insulin, lysozyme, progesterone, testosterone, TNF-α, transferrin, vitamin A, vitamin B1, vitamin B12, vitamin B6, vitamin D, vitamin K1, A-1-antitrypsin, histamine, tryptase and prostaglandin E2.

The faecal samples are stored at −80° C. until analysis. Faecal samples are subjected to 16S rRNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSF) information,
symptom information such as abdominal pain (as measured by the Numeric Rating Scale (NRS-11), abdominal discomfort, abdominal cramping, abdominal bloating, and abdominal fullness,
additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each patient has an exit visit with the medical team. Faecal samples and blood samples are collected and analysed as before.

The results show that oral ingestion of HMOs modulate the intestinal microbiota, and specifically stimulate the abundance of bifidobacteria. The blood biomarker analysis indicates that the treatment patients have reduced levels of inflammatory markers, and reduced release of mast cell mediators meaning stabilization of mast cells. Reduction in visceral pain and an improvement in bowel movement are reported by treatment patients as compared to the placebo group. Collectively, HMOs are able to increase bifidobacteria and stabilize mast cells, and hereby contribute to improvement in visceral pain in IBS patients.

Example 2—Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, HMSs/HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals and antioxidants, and meets FODMAP criteria. Further, the composition contains HMSs and/or HMOs which are able to promote the growth of beneficial intestinal bacteria and modulate chronic inflammation.

Example 3—Capsule Composition

A capsule is prepared by filling about 1 g of HMS/HMO into a 000 gelatine capsule using a filing machine. The capsules are then closed. The HMS/HMO are in free flowing, powder form.

Example 4—Mucosal Barrier Function

2'-FL and LNnT are tested with respect to their ability to induce MUC2, TFF3, EIMβ, CHST5, and GAL3ST2 expression in the human LS174T cell culture model of goblet cells. The human LS174T cell line is obtained from the American Type Culture Collection (ATCC). LS174T cells are maintained in minimum essential medium (MEM) supplemented according to instructions at 37° C. in 5% $CO_2$. 2'-FL and LNnT are dissolved in cell culture grade water to the required concentration. The LS174T cells are treated with the HMO solution containing 0 or 5 mg HMO/ml.

The LS174T cells are collected and suspended in Trizol reagent and total RNA is isolated using an RNA analysis kit (Qiagen) according to the manufacturer's instructions and the RNA isolates are quantified using Nanodrop analysis (Thermo Fisher Scientific). RNA isolates are reverse transcribed using a high capacity cDNA Reverse Transcription Kit (Applied Biosystems) to create cDNA, which is then used to assess gene expression via quantitative RT-PCR.

For the quantitative RT-PCR, specific TaqMAN gene expression assays are obtained from Applied Biosystems, which include expression assays for MUC2, TFF3, CHST5 and GAL3ST2. Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analysed using SDS 2.3 software and calculated by delta Ct method. All samples are normalized to Gus-β expression and fold induction is calculated over untreated controls. Gene expression is expressed as fold increase compared to HMO-free control cells. The experiment is repeated three times.

The results indicate that treatment with 2'-FL and LNnT increases the expression of the MUC2 and TFF3 genes compared to control cultures. Increased expression of goblet cell genes is specific and not universal, as evidenced by the minimal induction or lack of induction of CHST5 and GAL3ST2, respectively. MUC2 and TFF3 are key components of the mucosal barrier and improve mucosal barrier function.

The present disclosure may be embodied in other specific forms without departing from its spirit or essential characteristics. The described examples are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for reducing mast cell mediated visceral hypersensitivity and/or pain in a non-infant human, the method comprising:
   selecting an effective amount of one or more neutral human milk oligosaccharides (HMOs) selected from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human; and
   increasing the relative abundance of *Bifidobacterium adolescentis* in the gastrointestinal microbiota of the non-infant human and reducing the mast cell mediated visceral hypersensitivity and/or pain by administering to the non-infant human a daily dose of from about 3 g to about 10 g of the one or more HMOs.

2. The method of claim 1, wherein the non-infant human has intestinal bacterial overgrowth, dysbiosis and/or an impaired mucosal barrier.

3. The method of claim 1, wherein the non-infant human is an irritable bowel syndrome (IBS) patient.

4. The method of claim 1, further comprising improving gut barrier function of the non-infant human by administering to the non-infant human the daily dose of the one or more neutral HMOs.

5. The method of claim 1, wherein administering the one or more neutral HMOs comprises administering a mixture of:
   at least one fucosylated neutral HMO selected from 2'-FL, 3-FL, DFL, and LNFP-I; and
   at least one non-fucosylated neutral HMO selected from LNT and LNnT.

6. The method of claim 5, wherein the mass ratio of the fucosylated neutral HMOs to the non-fucosylated neutral HMOs in the mixture is from 4:1 to 2:1.

7. The method of claim 1, further comprising administering with the selected effective amount of the chosen one or more neutral HMOs, one or more additional HMOs selected from the group consisting of 3'-sialyllactose (3'-SL) and 6'-sialyllactose (6'-SL).

8. The method of claim 1, further comprising administering the selected amount of the chosen one or more neutral HMOs for an initial treatment period of from 1 week to 8 weeks.

9. The method of claim 8, further comprising, after the initial treatment period, administering a daily dose of from 1 g to 5 g of the chosen one or more neutral HMOs for a maintenance period of at least 1 month.

10. The method of claim 1, further comprising reducing looseness and/or frequency of bowel movements of the non-infant human by administering to the non-infant human the daily dose of the one or more HMOs.

11. A method for reducing mast cell mediated visceral hypersensitivity and/or mast cell mediated visceral pain in a non-infant human, the method comprising:
    selecting an effective amount of one or more neutral human milk oligosaccharides (HMOs) selected from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human;
    increasing the relative abundance of *Bifidobacterium adolescentis* in the gastrointestinal microbiota of the non-infant human and reducing the mast cell mediated visceral hypersensitivity and/or pain by administering to the non-infant human a daily dose of from about 3 g to about 10 g of the one or more neutral HMOs; and
    selectively increasing expression of intestinal goblet cell genes to improve mucosal barrier function in gastrointestinal tract of the non-infant human by administering to the non-infant human the daily dose of the one or more neutral HMOs.

12. The method of claim 11, wherein selectively increasing the expression of the intestinal goblet cell genes comprises selectively increasing the expression of MUC2 and/or TTF3 genes relative to the expression of CHST5 or GAL3ST2 goblet cell genes.

13. The method of claim 11, wherein for a maintenance treatment period of at least one month following the initial treatment period, the amount of the daily dose of the chosen one or more HMOs is from about 1 g to 5 g.

* * * * *